United States Patent [19]

Wegner et al.

[11] 4,107,312
[45] Aug. 15, 1978

[54] DISINFECTANT FOR USE IN CLOSED-CIRCUIT TOILET FLUSHING FLUIDS

[75] Inventors: Jürgen Wegner, Düsseldorf; Klaus Bansemir, Langenfeld; Othmar V. Ettingshausen, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 695,456

[22] Filed: Jun. 14, 1976

[30] Foreign Application Priority Data

Jun. 16, 1975 [DE] Fed. Rep. of Germany ....... 2526964

[51] Int. Cl.² .................... A01N 9/02; A01N 9/20; A01N 9/22; A01N 9/24
[52] U.S. Cl. .................................. 424/263; 424/76; 424/329; 424/333; 424/334; 424/342
[58] Field of Search ............... 424/76, 263, 329, 333, 424/334, 342

[56] References Cited

U.S. PATENT DOCUMENTS

| | | | |
|---|---|---|---|
| 2,998,390 | 8/1961 | Hamilton | 252/106 |
| 3,107,216 | 10/1963 | Hamilton | 210/60 |
| 3,208,936 | 9/1965 | Hamilton | 252/1 |
| 3,282,775 | 11/1966 | Stonebili | 424/333 X |
| 3,505,690 | 4/1970 | Lockwood | 4/115 |
| 3,785,971 | 1/1974 | Halley | 210/64 |

*Primary Examiner*—Allen J. Robinson
*Attorney, Agent, or Firm*—Hammond & Littell

[57] ABSTRACT

Compositions consisting essentially of:

| Component | Weight % |
|---|---|
| Formaldehyde | 5–20 |
| Glyoxal | 0–1.5 |
| Glutaraldehyde | 2–13 |
| Quaternary ammonium bactericide | 0.5–5 |
| Wetting agent | 0–5 |
| Scent | 0–5 |
| Dye | 0–1 |
| Solvent | Remainder | possess excellent bactericidal efficiency yet possess little tendency, in dilute aqueous solution, to corrode aluminum and its alloys. They are therefore suitable for use as disinfecting agents in closed circuit aircraft type toilets made of aluminum which operate with aqueous flushing liquids.

5 Claims, No Drawings

DISINFECTANT FOR USE IN CLOSED-CIRCUIT TOILET FLUSHING FLUIDS

The invention relates to compositions useful as disinfectants in the circulating flushing fluid of closed-circuit toilet systems at least partly constructed of aluminum and alloys thereof.

At the present time, closed circuit toilets are in general use in aircraft, yachts, local service ships, trailers and other conveyances where an adequate supply of water for flushing is not available or where discharge of sewage is not permitted. The mode of operation of closed circuit toilets is such that a flushing liquid is taken from a sewage holding tank for each flushing operation and, after passage through a filter, is pumped into the tiolet bowl, thereby flushing the toilet, the bowl effluent being piped to the holding tank. In order to prevent bacterial growth in the fluid, a disinfectant is added to the fluid. The disinfectant generally includes a deodorant and a dye to provide the fluid with a pleasing color. In order to extend the reaction time of the disinfectant, the circulation system can be equipped with an intermediate holding tank (or series of intermediate holding tanks) in which the flushing liquid (containing the disinfectant) is allowed to stand after passage through the filter. Such a tiolet system is disclosed and claimed in Bansemir et al. U.S. pat. application Ser. No. 558,203, filed on Mar. 14, 1975, now abandoned.

High demands are made on the disinfecting power of the disinfectant and on the compatibility of the disinfectant with the metals present in tiolet fluid transfer systems. Corrosion is particularly important in connection with the light metals and light metal alloys which are frequently used in tiolet systems intended for use in aircraft. Hitherto, the requirement with respect to a rapid and prolonged disinfecting action, and a wide spectrum of effectiveness could not be satisfactorily met with optimum compatibility of the disinfectants for the light metals present in the system. Thus, despite the presence of corrosion inhibitors in the flushing liquid an inadequate disinfecting action frequently had to be accepted.

It is a principal object of the invention to provide a composition which is a rapidly effective and long-lasting biocide and which, at the dilutions present in aqueous toilet flushing fluids, possesses negligible tendency to corrode aluminum and its alloys.

It is a further object of the invention to provide such compositions in high concentration fluid form which will permit them to be dosed conveniently into the flushing liquid by automatic dosing devices.

It is a further object to provide such compositions which do not require a volatile, inflammable or corrosive solvent.

It has now been discovered that certain aldehyde-quaternary ammonium compound mixtures are powerful and long-lasting biocides which act with great rapidity, and it has further been found that these mixtures possess at most a negligibly low capacity to corrode aluminum and its alloys when present in dilute aqueous medium.

We have found that in preferred instances these compositions, at the concentrations at which they are normally present in aqueous toilet flushing liquids, possess the capability of decreasing the concentration of live microbes in sewage by 99.9% in 10 minutes at room temperature and to produce no more than a negligible amount of corrosion to aluminum and its alloys.

The compositions of the present invention thus can be safely present in aqueous flushing systems circulating in aluminum systems, without need for a corrosion inhibitor.

They can also be successfully used in circulatory toilet systems fabricated from magnesium and its alloys, but there the solution causes corrosion at a moderate rate.

These findings are unexpected in that previously known disinfectants based on aldehydes have generally required special corrosion inhibitors when used in toilet systems fabricated from light metals.

Accordingly this invention provides disinfectants for circulation toilets, consisting essentially of

| Component | % By Weight |
| --- | --- |
| Formaldehyde ($CH_2O$) | 5 - 20 |
| Glyoxal (CHO–CHO) | 0 - 1.5 |
| Glutaraldehyde CHO–$(CH_2)_3$–CHO | 2 - 13 |
| Quaternary ammonium biocide | 0.5 - 5 | in an aqueous or aqueous/alcoholic solution form.

The solvent may be water or a mixture of water with one or more hydrophilic organic solvents.

Suitable quaternary ammonium salts having a disinfecting action are, in particular, compounds having a quaternary nitrogen atom and at least one $C_6$–$C_{20}$ alkyl or alkylphenyl radical (optionally substituted by a halogen), for example dodecyl trimethyl ammonium chloride, dodecyl dimethyl benzyl ammonium chloride, dodecyl pyridinium chloride, (dichlorobenzyl) dimethyl dodecyl ammonium chloride, and p-dodecylbenzyl trimethyl ammonium chloride) also known as "Halimide®." Preferably, benzyl trimethyl ammonium chloride is used. A mixture of these compounds can be used. The higher members of the series possess the advantage of acting as surface-active agents.

The composition can contain a small proportion of methanol as stabilizer for the formaldehyde.

The disinfectant compositions of the present invention may and preferably do contain such other components as are customarily present in aqueous toilet flushing solutions, so long as they do not alter the essential character of the disinfectant. Thus the compositions may contain conventional amounts of dyes to alter or mask the color of the flushing liquid, scents or similar materials to mask the odor of the flushing fluid, and cationic or non-ionic wetting agents, to improve the flushing properties of the fluid.

Suitable wetting agents are, in particular, non-ionic ethylene oxide adducts of higher fatty alcohols or alkyl phenols having 8 to 22 carbon atoms. They are present in quantities from 0 up to 5% and preferably 0.5 to 2% of the weight of the composition.

The disinfectants are provided in dry form or in the form of aqueous or aqueous/alcoholic solutions. Suitable alcoholic solvents are glycols having 2 to 4 carbon atoms and aliphatic alcohols having 1 to 4 carbon atoms, which may be present in a quantity of up to 50% by weight of the total solvent component.

The aforesaid solutions are suitable for use in closed circuit toilets provided with automatic disinfectant dosing means.

The scents can be present in olfactorily tolerable amount, that is, up to about 5%.

The dyes can be present in tinctorially effective amount, that is, up to about 5%.

The disinfectants of the invention are suitable for use in closed circulation toilet systems in railway trains, busses, trailers, country and beach cottages, yachts and the like. Owing to the negligible extent to which they corrode aluminum and its alloys, they can be used to particular advantage as the disinfecting agent in aircraft toilets constructed of this metal. Unexpectedly, it has been found that it is unnecessary to use special anticorrosion agents.

For use, a quantity of from 2 to 35 grams per liter of flushing fluid of the disinfecting solution is introduced into the flushing fluid at any convenient point in the cycle, for example at the intermediate holding tank. Preferably, 10 to 20 g./l. is introduced. Alternatively, however, a smaller quantity of the solution can be metered into the flushing circuit and/or into the tank by means of a metering device during each flushing operation, so that the disinfecting agent is maintained at a biocidally effective level, within the range of 0.1 and 5% by weight based on the amount of solution added, or 0.01 to 5% based on the total weight of the aldehydes and biocide.

When the agent is present in this range, the number of germs in the flushing liquid are reduced to a considerable extent (by at least 3 powers of 10, i.e., by 99.9%) within 10 minutes.

The invention is further illustrated by the examples which follow. These examples are best embodiments of the invention and are not to be construed in limitation thereof.

The comparative efficiencies of the disinfectant compositions of the present invention with respect to the reduction of the concentration of germs and the compatibility of solutions of the compositions with respect to aluminum and magnesium alloys were determined in the following manner.

1. Bactericidal Efficiency (Excrement Suspension Test)

50 ml. of the disinfecting solution diluted to 1% solids with water is mixed with 10 g. of excrement in an agitator flask, and the decrease in the concentration of organisms which occurs after 10 minutes is determined by the Koch plate method (using dilution water containing a deinhibiting agent, e.g. histidine).

2. Corrosiveness to Light Metal (Sandwich Test on Aluminum Alloy

The test is performed on Al-Clad (2024 T 3) sheet in accordance with Douglas Aircraft Company procedure (CSD No. 3, Sect. 3, May 1, 1974), as follows. A sheet of filter paper saturated with the disinfecting solution as prepared is sandwiched between two degreased and cleaned aluminum plates, and the assembly is placed in an air-conditioned cabinet at specified relative humidity and temperature for 7 days. The test plates were inspected by naked eye and under a microscope and were compared with the control plates, and the surface corrosion was assessed. The procedure was repeated with the solution diluted to 5% solids with water, and was again repeated using artificial city water as control.

3. Magnesium Corrosion Test

A degreased and cleaned magnesium plate (specification AMS 4375) which had been roughened with emery paper is weighed, completely immersed for 60 hours at room temperature in the disinfecting solution as prepared, cleaned by immersion for 10 seconds in 0.3N $H_2SO_4$, rinsed, dried, and reweighed, and the loss of weight determined. The procedure is repeated using the solution diluted to 5% solids with water.

EXAMPLE 1

A highly effective disinfectant which is substantially non-corrosive to light metals is prepared as follows:

| Component | % by Weight |
|---|---|
| Formaldehyde | 8.45 |
| Glyoxal | 0.20 |
| Glutaraldehyde | 6.45 |
| Benzyl trimethyl ammonium chloride | 3.0 |
| Wetting agent (cond. product of 1 mol of nonylphenol with 8 mols of ethylene oxide) | 1.9 |
| Dye (inert) Marine Blue BNX | 0.125 |
| Scent (inert) | 3.0 |
| Water, deionized | Remainder |

The principal properties of the composition are determined as described above, with the following results.

| Bactericidal Efficiency (Excrement Suspension Test) |
|---|
| The total number of colonies was reduced from $11 \times 10^7$ to $1 \times 10^3$ colonies/ml. within 10 minutes at 20° C. |

| Corrosiveness to Light Metal (Sandwich Test on Aluminum Alloy) | | |
|---|---|---|
| Undiluted | 5% Aqueous Dilution | City Water |
| Slight | Very slight | Very slight |

| Magnesium Corrosion Test (Loss of Weight After 60 Hours Of Contact at Room Temperature) | |
|---|---|
| Solution | |
| Undiluted | 5% Aqueous Dilution |
| 0.76% | 0.81% |

EXAMPLE 2

A highly effective disinfectant which is substantially non-corrosive to light metal is prepared as follows.

| Component | % by Wt. |
|---|---|
| Formaldehyde | 12.9 |
| Glyoxal | 0..4 |
| Glutaraldehyde | 6.75 |
| Dodecyl trimethyl ammonium chloride | 3.0 |
| Wetting agent (cond. product of 1 mol of nonylphenol with 8 mols of ethylene oxide) | 1.9 |
| | 1.9 |
| Dye (Marine Blue BNX) | 0.125 |
| Scent (inert) | 3.0 |
| Water, deionized | Remainder |
| Total | |

The principal properties of the composition are determined as described above, with the following results.

| Bactericidal Efficiency (Excrement Suspension Test) |
|---|
| The total number of colonies was reduced from $7 \times 10^7$ to $7 \times 10^2$ colonies/ml. within 10 minutes |

-continued at 20° C.

Corrosiveness to Light Metal
(Sandwich Test on Aluminum Alloy)

| Undiluted | 5% Aqueous Dilution | Water Control |
|---|---|---|
| Very slight | Very slight | Very slight |

Magnesium Corrosion Test
(Loss of Weight After 60 Hours
Of Contact at Room Temperature)

| Solution | |
|---|---|
| Undiluted | 5% Aqueous Dilution |
| 0.85% | 0.88% |

EXAMPLE 3

A disinfectant having a very good disinfecting power and good to adequate compatibility with light metal comprises:

| Component | % by Weight |
|---|---|
| Formaldehyde | 12.7 |
| Glyoxal | 1.0 |
| Glutaraldehyde | 10.7 |
| Dodecyl pyridinium chloride | 4.3 |
| Wetting agent (cond. prod. of 1 mol of nonylphenol with 8 mols of ethylene oxide) | 1.9 |
| Dye (marine blue BNX) | 0.125 |
| Scent | 3.0 |
| Water, deionized | Remainder |

The principal properties of the composition are determined as described above, with the following results.

Batericidal Efficiency
(Excrement Suspension Test)

The total number of colonies was reduced from $1 \times 10^7$ to $7 \times 10^2$ colonies/ml. within 10 minutes at 20° C.

Corrosiveness to Light Metal
(Sandwich Test on Aluminum Alloy)

| Undiluted | 5% Aqueous Dilution |
|---|---|
| Slight to moderate | Slight |

Magnesium Corrosion Test
(Loss of Weight After 60 Hours
Of Contact At Room Temperature)

| Solution | |
|---|---|
| Undiluted | 5% Aqueous Dilution |
| 3.65% | 1.3% |

The foregoing examples show that the disinfectant compositions of the present invention completely fulfil the requirement with respect to rapid disinfecting action, namely the reduction of the total number of colonies by at least 3 powers of 10 within 10 minutes, and at the same time are compatible with the aluminum used in aircraft construction. In particular, the presence of corrosion inhibitors is not required in the flushing fluid.

EXAMPLE 4

The following illustrates the preparation and use of a dry blend of a disinfecting composition according to the present invention in substantially anhydrous form.

The following materials are placed in a flask under a blanket of dry nitrogen gas and mixed until uniform.

| Component | Grams |
|---|---|
| Paraformaldehyde | 100 |
| Glyoxal, dihydrate | 20 |
| Glutaraldehyde | 90 |
| (p-Dodecylbenzyl) trimethyl ammonium chloride | 20 |
| Solution aid (sodium sulfate) | 10 |
| Total | 240 |

The mixture is then bottled. It remains stable at room temperature for a month.

The mixture is then added to the water charged into a circulating toilet starting a fresh cycle to provide 1% of total aldehydes on the weight of the flushing fluid. The circulating fluid remains sanitary during several weeks.

We claim:

1. A solution suitable for disinfecting the circulating fluid in a closed-circuit toilet system consisting essentially of:

| Component | Weight % |
|---|---|
| Formaldehyde | 5-20 |
| Glyoxal | 0-1.5 |
| Glutaraldehyde | 2-13 |
| Quaternary ammonium biocide, water-soluble, selected from the group consisting of benzyl trimethyl ammonium chloride, benzyl dimethyl dodecyl ammonium chloride, dichlorobenzyl dimethyl dodecyl ammonium chloride, dodecyl trimethyl ammonium chloride, dodecyl pyridinium chloride, and (p-dodecylbenzyl) trimethyl ammonium chloride | 0.5-5 |
| Inert scent | 0-5 |
| Non-ionic ethylene oxide adducts of higher fatty alcohols or alkyl phenols having 8 to 22 carbon atoms | 0-5 |
| Inert dye | 0-5 |
| Solvent selected from the group consisting of (i) water and (ii) a mixture of water and an alcohol selected from the group consisting of glycols having 2 to 4 carbon atoms and aliphatic alcohols having 1 to 4 carbon atoms | Remainder. |

2. A solution according to claim 1 consisting essentially of:

| Component | Weight % |
|---|---|
| Formaldehyde | 5 -20 |
| Glyoxal | 0 -1.5 |
| Glutaraldehyde | 2 -13 |
| Quaternary ammonium biocide | 0.5- 5 |
| Non-ionic ethylene oxide adducts of higher fatty alcohols or alkyl phenols having 8 to 22 carbon atoms | 0.5 - 2 |
| Inert scent | 0.5 - 2 |
| Inert eye | 0.5 - 2 |
| Solvent | Remainder. |

3. A solution according to claim 1 wherein the non-ionic ethylene oxide adduct is the condensation product of 1 mole of nonyl phenol with 8 moles of ethylene oxide.

4. A disinfectant solution according to claim 1 wherein the solvent is water.

5. A substantially anhydrous composition suitable for disinfecting the circulating fluid in a closed toilet system, consisting essentially of:

| Component | Parts by Weight |
|---|---|
| Paraformaldehyde | 5 – 20 |
| Glyoxal dihydrate | 0 – 2.3 |
| Glutaraldehyde | 2 – 13 |
| Quaternary ammonium biocide, water-soluble, selected from the group consisting of benzyl trimethyl ammonium chloride, benzyl dimethyl dodecyl ammonium chloride, dichlorobenzyl dimethyl dodecyl ammonium chloride, dodecyl, dodecyl pyridinium chloride, and (p-dodecylbenzyl) trimethyl ammonium chloride | 0.5 – 5 |
| Non-ionic ethylene oxide adducts of higher fatty alcohols or alkyl phenols having 8 to 22 carbon atoms | 0 – 5 |
| Inert dye | 0 – 5 |
| Inert scent | 0 – 5 |

* * * * *